US010485671B2

(12) United States Patent
Moradi et al.

(10) Patent No.: US 10,485,671 B2
(45) Date of Patent: Nov. 26, 2019

(54) PROSTHESIS FOR DISTAL RADIOULNAR JOINT

(71) Applicants: Ali Moradi, Mashhad (IR); Ehsan Vahedi, Mashhad (IR); Saeed Kermani, Mashhad (IR); Mohammad Hosein Ebrahimzadeh, Mashhad (IR); Golnaz Ghayyem Hassankhani, Mashhad (IR); Nahid Mojaver, Mashhad (IR)

(72) Inventors: Ali Moradi, Mashhad (IR); Ehsan Vahedi, Mashhad (IR); Saeed Kermani, Mashhad (IR); Mohammad Hosein Ebrahimzadeh, Mashhad (IR); Golnaz Ghayyem Hassankhani, Mashhad (IR); Nahid Mojaver, Mashhad (IR)

(*) Notice: Subject to any disclaimer, the term of this patent is extended or adjusted under 35 U.S.C. 154(b) by 75 days.

(21) Appl. No.: 15/917,871

(22) Filed: Mar. 12, 2018

(65) Prior Publication Data

US 2018/0200069 A1  Jul. 19, 2018

Related U.S. Application Data

(60) Provisional application No. 62/470,347, filed on Mar. 13, 2017.

(51) Int. Cl.
*A61F 2/42* (2006.01)
*A61F 2/30* (2006.01)

(52) U.S. Cl.
CPC .. *A61F 2/4261* (2013.01); *A61F 2002/30331* (2013.01); *A61F 2002/30507* (2013.01);
(Continued)

(58) Field of Classification Search
CPC .............. A61F 2/4261; A61F 2/3804; A61F 2002/30642; A61F 2002/4269;
(Continued)

(56) References Cited

U.S. PATENT DOCUMENTS 3,992,726 A * 11/1976 Freeman ............... A61F 2/4225
623/23.4
5,314,485 A  5/1994 Judet
(Continued)

FOREIGN PATENT DOCUMENTS

CN  105250055 A  1/2016

OTHER PUBLICATIONS

APTIS, The Scheker Distal Radio-Ulnar Joint Prosthesis, Technical guide, 27 pages.
(Continued)

*Primary Examiner* — Brian A Dukert
(74) *Attorney, Agent, or Firm* — Bajwa IP Law Firm; Haris Zaheer Bajwa

(57) ABSTRACT

A method and a device for replacing radioulnar joint are disclosed. The method may include inserting a distal stem into a distal part of the ulna bone, and inserting a proximal stem into the proximal part of the ulna bone. In addition, the method may include inserting a stem insertion part located at a proximal end of a mobile locker into the cylindrical-shaped opening of the proximal stem. The method further includes twisting the mobile locker so that the first semicircle-shaped opening and the second semicircle-shaped opening are aligned such that a spherical cavity is formed between the mobile locker, and inserting a mobile globe into the spherical cavity. The method may also include twisting the mobile locker so that the first semicircle-shaped opening and the second semicircle-shaped opening are misaligned and the mobile globe is secured within the spherical cavity, (Continued)

and securing the mobile locker into a substantially fixed position relative to the proximal stem by tightening one or more of a plurality of screws in a plurality of threaded holes.

12 Claims, 5 Drawing Sheets

(52) U.S. Cl.
CPC ............... *A61F 2002/30594* (2013.01); *A61F 2002/30642* (2013.01); *A61F 2002/4269* (2013.01); *A61F 2310/00017* (2013.01); *A61F 2310/00023* (2013.01); *A61F 2310/00029* (2013.01)

(58) Field of Classification Search
CPC ............. A61F 2002/2896; A61B 17/72; A61B 17/7291; A61B 17/7216; A61B 17/7225
See application file for complete search history.

(56) References Cited

U.S. PATENT DOCUMENTS

| | | |
|---|---|---|
| 6,302,915 B1 | 10/2001 | Cooney, III et al. |
| 7,918,894 B2 | 4/2011 | Wolfe et al. |

OTHER PUBLICATIONS

Small Bone Innovations, uHead ulnar implant system, surgical technique, 12 pages.
INTEGRA, Universal2-total wrist implant system, surgical technique, 10 pages.

\* cited by examiner

PROSPTHESIS FOR DISTAL RADIOULNAR JOINT

CROSS-REFERENCE TO RELATED APPLICATION

This application claims the benefit of priority from pending U.S. Provisional Patent Application Ser. No 62/470,347, filed on Mar. 13, 2017, and entitled "DISTAL RADIO-ULNAR JOINT (DRUJ) PROSTHESIS" which is incorporated herein by reference in its entirety.

TECHNICAL FIELD

The present disclosure generally relates to prostheses, and particularly to distal radioulnar joint prostheses, and more particularly to devices and methods that are used in implanting a distal radioulnar joint prosthesis.

BACKGROUND

The distal radioulnar joint is a "shallow socket" ball joint. The radius articulates in pronation and supination on the distal ulna. The ulna, a relatively straight forearm bone linked to the wrist, translates dorsal-palmarly to accept the modestly bowed radius. Since the sigmoid fossa socket in most wrists is relatively flat, ligaments are required to support the distal ulna. These ligaments include the triangular fibrocartilage (TFC), the extensor carpi ulnaris (ECU) subsheath, and the ulnar collateral ligament complex. The stabilizing elements of the triangular fibrocartilage (TFC), extensor carpi ulnaris (ECU) subsheath, and the ulnar collateral ligament complex are well recognized along with the importance of a distal ulna component (ulnar head) for transfer of compressive loads between the ulnar carpus and the distal ulna across the distal radioulnar joint.

Ligament disruption, ulnar styloid fractures, and fractures into the distal radioulnar joint are common occurrences following fractures of the distal radius and other rotational instability injuries of the forearm. Fracture or dislocation involving the distal radioulnar joint often results in a loss of forearm rotation related to either instability or incongruity between the sigmoid fossa of the distal radius and the ulnar head. A variety of different fractures involving the distal radius may cause this condition including the Colles' fracture and the Galeazzi fractures. When there is loss of stability of the distal radioulnar joint, there is subsequent weakness in grip and pinch as well as potential loss of forearm rotation. Instability may also be associated with either an injury to the triangular fibrocartilage or to the ulnar styloid. As instability is present, a number of ligament reconstructive procedures have been devised to assist in treating the unstable distal ulna. Unfortunately, ligament reconstruction of the distal ulna is often incomplete in restoring stability, and joint replacement is often necessary.

Where there is an incongruity of the joint surface involving either the articulation of the ulnar head with the sigmoid fossa of the distal radius, or if there is a significant ulnar impaction syndrome between the distal articular surface of the head of the ulna and the ulna carpus, a joint replace may be necessary. Specifically, this may include either joint replacement of the distal ulna or operative procedures designed to shorten the ulna or resect all or part of the distal ulna. Unfortunately, there have been variable results associated with the partial or complete resections of the distal ulna, particularly those performed by open resection. For example, when the ulna is resected, and not replaced with a prosthesis, both instability of the wrist and "snapping" of the forearm in rotational pronation/supination may occur.

The primary indications, therefore, for reconstruction of the distal radioulnar joint by prosthetic replacement are generally related to a fracture of the distal ulna or a fracture extending into the distal radioulnar joint producing post-traumatic arthritis. Degenerative arthritis from other causes is also a primary indication. This is considered if there is associated arthritis and an ulnar shortening procedure is contraindicated. A third condition for primary ulna replacement is rheumatoid arthritis with a painful and unstable distal radioulnar joint. In these situations, prosthetic replacement of the distal ulna with soft tissue advancement may be beneficial.

A distal ulnar prosthesis is also suitable to correct a previous resection of the distal ulna that has failed. Such will be the case for 1) partial resection of the joint articular surface, or 2) complete resection of the distal ulna. When face with the failed distal ulna resection, one has options towards reconstruction without restoring the distal radioulnar joint. For example, a failed distal ulna may be corrected by a pronator quadratus interposition, or, if there has been only a partial resection, a fusion of the distal radioulnar joint combined with a proximal pseudarthrosis.

These procedures, however, do not restore the normal distal radioulnar joint function of motion or load transfer and are also associated with some drawbacks. For example, there are difficulties in retaining stability of the distal ulna and proximal impingement of the ulna on the distal radius. In addition, movements of the forearm causes a slipping movement of the metallic prosthesis on the ulna/radius bone that may cause to prosthesis wear. There is, therefore, a need in the art for intraosseous artificial prosthesis for distal radioulnar joint that is able to retain stability of the distal ulna and proximal impingement of the ulna on the distal radius and prevents the prosthesis wearing during forearm motions.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for implanting an artificial prosthesis in forearm of a patient. The method may include inserting a distal stem into a distal part of the ulna bone, and inserting a proximal stem into the proximal part of the ulna bone. The distal stem may include a distal bone insertion part located at a distal end of the distal stem. The distal stem may further include a distal base located at a proximal end of the distal stem.

In some exemplary implementations, the distal bone insertion part may have a plug-shaped profile. In some alternative implementations, the distal bone insertion part may have a shape that is defined by having a substantially circular profile, a substantially elliptical profile, a substantially parabolic profile, or any other similar profiles In some exemplary implementations, the distal base may include a first mobile globe holding section comprising a first half-spherical surface with a largest circumference at a proximal end of the distal stem. The distal base may further include a first outer band located at the proximal end of the distal stem including a first semicircle-shaped opening from a side-view perspective of the first mobile globe holding section.

In some implementations, the proximal stem may include a proximal bone insertion part located at a proximal end of the proximal stem. The proximal stem may also include proximal base located at a distal end of the proximal stem. In some implementations, the proximal bone insertion part may include a circular profile. In some alternative implementations, the proximal bone insertion part may include a shape that having a substantially plug-shaped profile, a substantially elliptical profile, a substantially parabolic profile, or any other similar profiles.

In some exemplary implementations, the proximal base may include a second outer band comprising a plurality of threaded holes. The Proximal base may further include a plurality of screws in which each respective screw in the plurality of screws may be associated with a respective threaded hole of the plurality of holes, and also each respective threaded hole may be tightened by the insertion of the associated respective screw. In some implementations, the proximal stem may further include a cylindrical-shaped opening located at the distal end of the proximal stem.

In some implementations, the method may further include dividing the ulna bone into a proximal part and a distal part by removing a segment of the ulna bone in a way such that the proximal part is connected to a proximal radioulnar joint and the distal part is connected to a distal radioulnar joint.

In one exemplary implementation, the method includes inserting a stem insertion part located at a proximal end of a mobile locker into the cylindrical-shaped opening of the proximal stem. In some implementations, the mobile locker may further include a mobile locker base located at a distal end of the mobile locker. In an exemplary implementation, the mobile locker base may include a second mobile globe holding section comprising a second half-spherical surface with the largest exposed surface area at a proximal end of the mobile locker.

In some implementations, the method further includes twisting the mobile locker so that the first semicircle-shaped opening and the second semicircle-shaped opening are aligned such that a spherical cavity is formed between the mobile locker and the distal stem, and inserting a mobile globe into the spherical cavity.

In one exemplary implementation, the method further includes twisting the mobile locker so that the first semicircle-shaped opening and the second semicircle-shaped opening are misaligned and the mobile globe is secured within the spherical cavity.

In one exemplary implementation, the method further includes securing the mobile locker into a substantially fixed position relative to the proximal stem by tightening one or more of the plurality of screws in the plurality of threaded holes.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1:
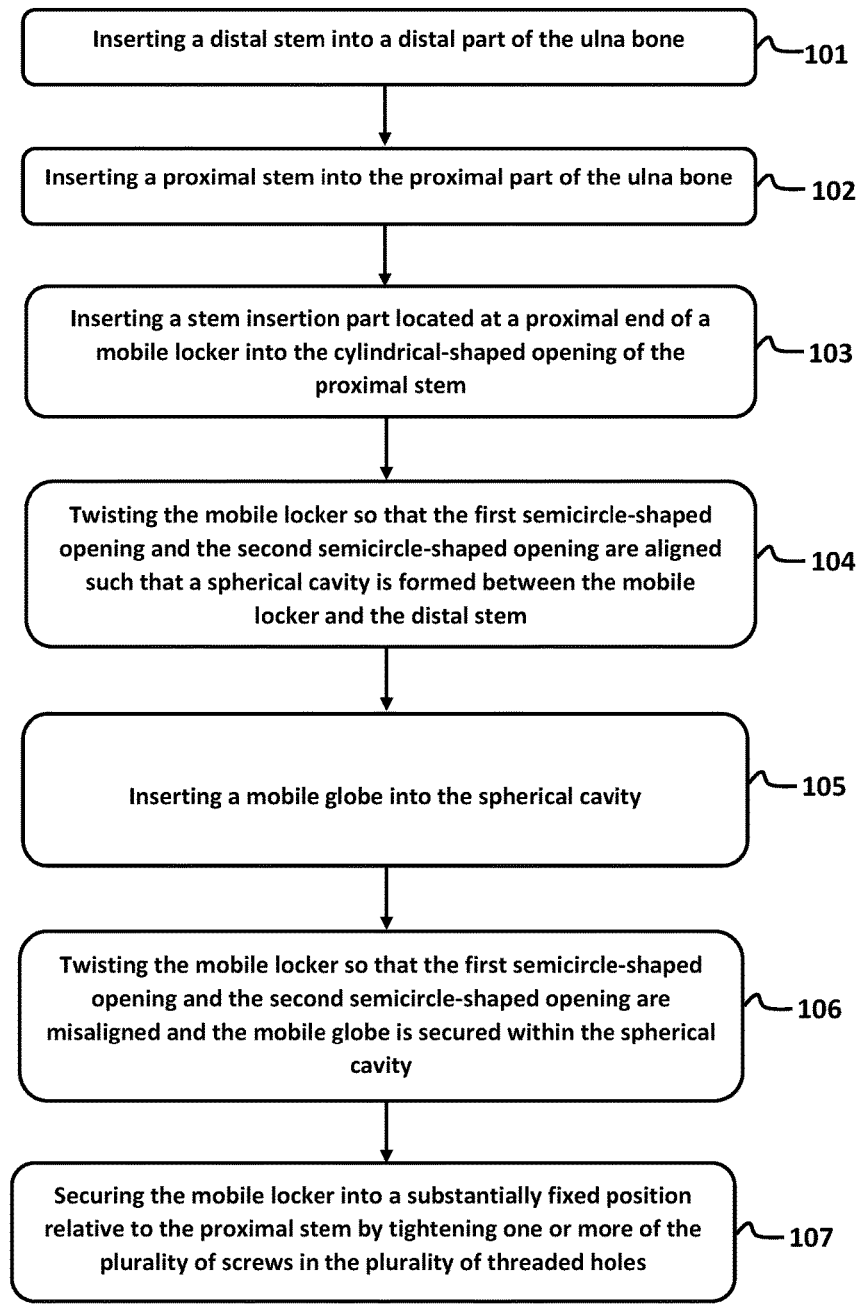
FIG. 1 illustrates a method for implanting an artificial prosthesis in forearm of a patient, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Wrist implants, generally, include two components, namely, a distal component (or carpal component) and a proximal component (or radial component). Typically conventional wrist implants include a somewhat elliptical shaped convex distal component that articulates with a similarly shaped concave radial component. While these implants readily allow rotations about the two major orthogonal axes, coinciding with classically and anatomically defined wrist motions of flexion-extension and radio-ulnar deviation, these implants do not readily permit wrist motions that are oblique to these orthogonal axes, for example a dart thrower's motion. The dart thrower's motion is about an axis that is a combination of both flexion-extension and radial-ulnar deviation.

The following disclosure describes techniques and systems for use of distal radioulnar joint prosthesis that allow a patient to perform wrist motions that are oblique to these orthogonal axes, for example the dart thrower's motion, without restraint from the implant. The systems are designed to more readily provide some movements of forearm and wrist for a patient suffering from a pain in distal radioulnar joint. As will be discussed below, such systems and methods may allow significant improvement and ease-of use in the operation of distal radioulnar joint prosthesis by offering the stable application of some degrees of freedom.

For purposes of reference, it should be understood that the techniques and systems disclosed herein are applicable to coupled motion in a wrist; however, the techniques and systems may be adapted to a number of other applications, including knee joints, elbow joints, or any other joints that require a wide variety of complex movements and/or their combination.

In some implementations, the disclosed artificial prosthesis may include a distal stem, a proximal stem, a mobile locker, and a mobile globe. The distal stem of the artificial prosthesis may be inserted into a medullary cavity of a distal part of the ulna bone. Similarly, a proximal stem of the artificial prosthesis, may be inserted into the medullary cavity of a proximal part of the ulna bone. For purpose of references, it should be understood that in some exemplary implementations, the ulna bone may be divided into a proximal part of the ulna bone and a distal part of the ulna bone by, for example, removing a segment of the ulna bone.

Afterwards, in some implementations, a spherical object may be inserted into a spherical cavity formed in combination by a part of the distal stem along with a part of the mobile locker placed within the proximal stem. Specifically, in some exemplary implementations, the mobile locker and the distal stem may be rotated in such an arrangement that by rotating the mobile locker in a specific direction and by a specific amount, a circular opening is formed, allowing for the mobile globe to be inserted into the spherical cavity. Thereafter, by rotating the mobile locker further, the alignment of the distal stem and the mobile locker may be changed, so that the mobile globe is prevented from going out from the spherical cavity. Implanting the disclosed artificial prosthesis into the ulna bone may provide significant benefits, including but not limited to, increased maneuverability of the forearm, for example, allowing rotation of the forearm and pronation/supination of the wrist.

Figure 2A:
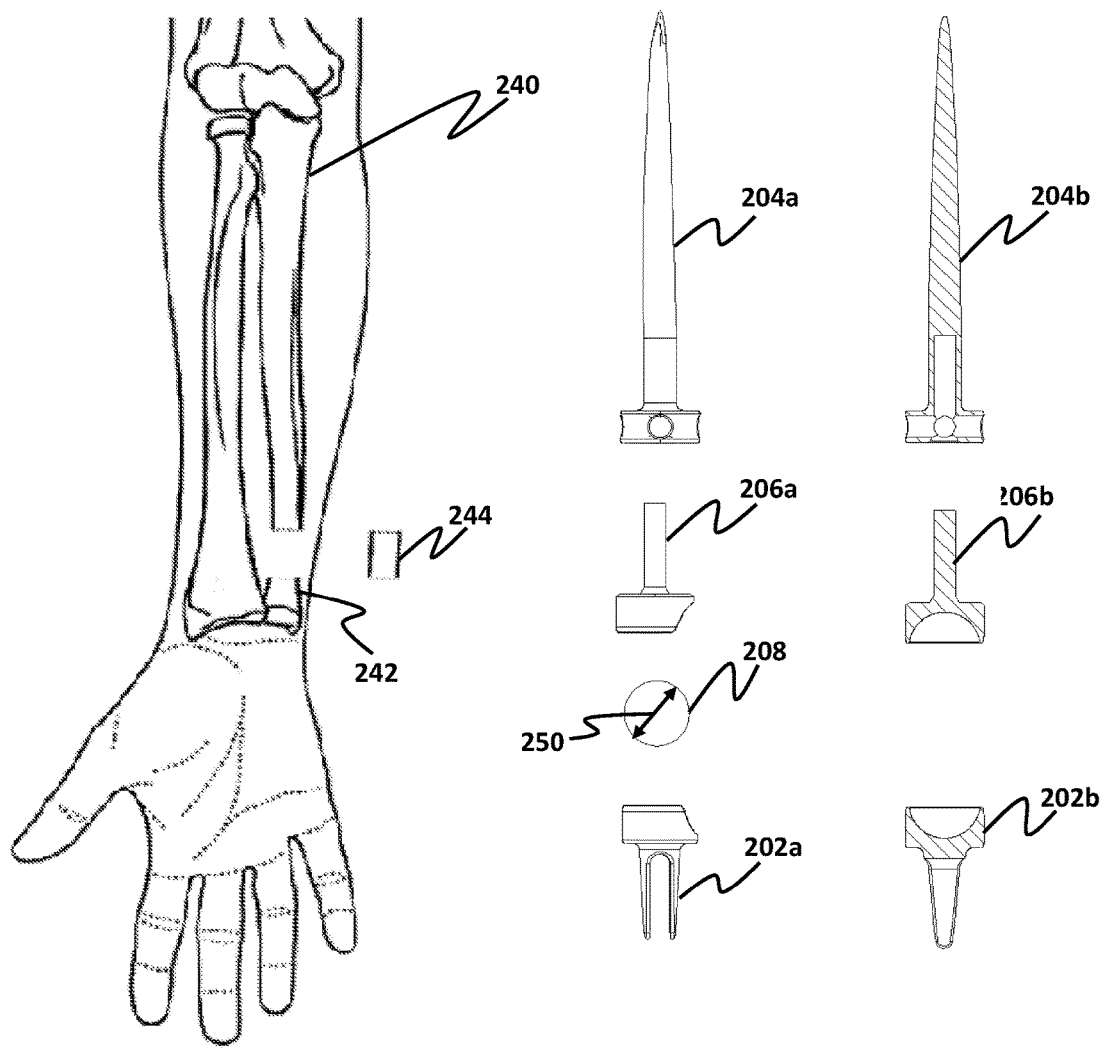
FIG. 2A illustrates a schematic view of an ulna bone and components of an artificial prosthesis, consistent with one or more exemplary embodiments of the present disclosure.
Figure 2B:
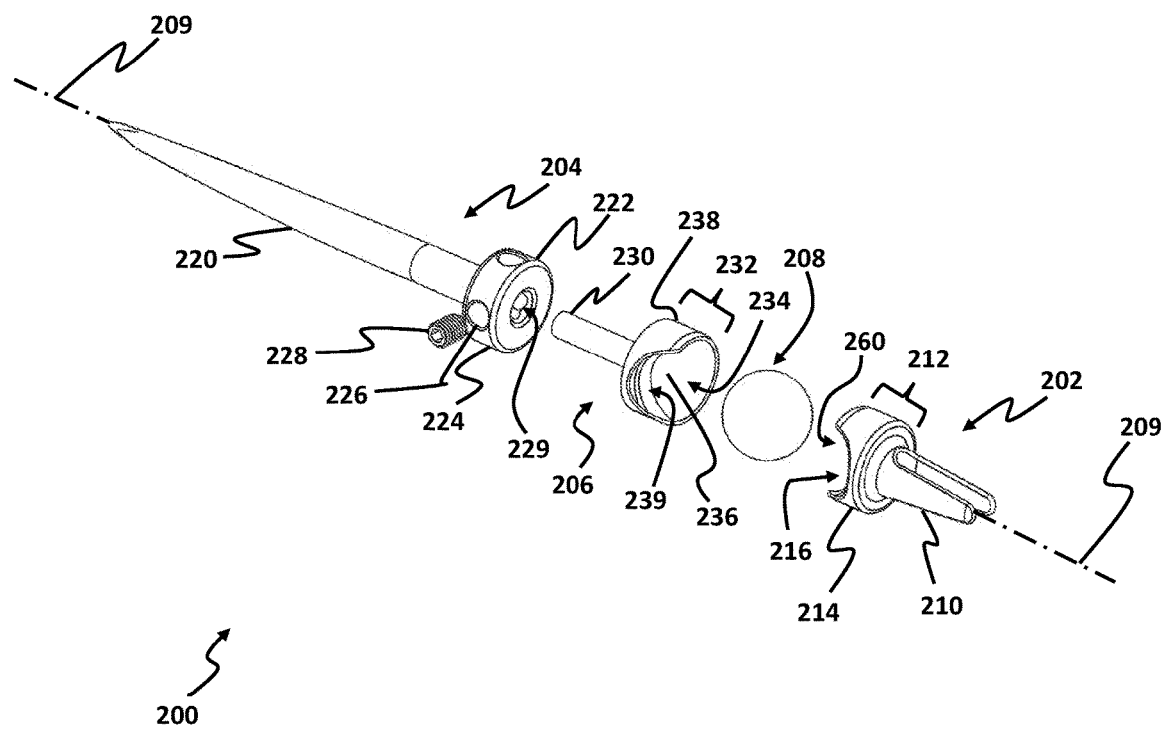
FIG. 2B illustrates a detailed view of an artificial prosthesis, consistent with one or more exemplary embodiments of the present disclosure.

Referring now to FIGS. 1, 2A, and 2B, a method 100 for implanting an artificial prosthesis in forearm of a patient is illustrated in combination with structural elements displayed in FIGS. 2A and 2B, consistent with one or more exemplary embodiments of the present disclosure. In some exemplary implementations, the method 100 may utilize an artificial prosthesis that includes a distal stem, a proximal stem, a mobile locker, and a mobile globe. As shown in FIG. 1, the method 100 includes step 101 of inserting a distal stem into a distal part of the ulna bone, and step 102 of inserting a proximal stem into the proximal part of the ulna bone. As shown in FIGS. 2A and 2B, in some exemplary implementations, the distal stem utilized in step 101 of the method 100 may be substantially similar to distal stem 202. In some implementations, distal stem 202 may include distal bone insertion part 210 located at a distal end of distal stem 202. Distal stem 202 may further include distal base 212 located at a proximal end of distal stem 202. In some exemplary implementations, distal base 212 may include a first mobile globe holding section 260 comprising a first half-spherical surface (obscured from the view in FIG. 2B) with a largest circumference at a proximal end of the distal stem 202. Distal base 212 may further include a first outer band 214 located at the proximal end of the distal stem 212 including a first semicircle-shaped opening 216 from a side-view perspective of the first mobile globe holding section 260. In some exemplary implementations, distal bone insertion part 210 may have a plug-shaped profile. In exemplary embodiments, profile may refer to a shape or physical appearance of an object or part of the object. However, in some alternative implementations, the distal bone insertion part 210 may have a shape that is defined by having a substantially circular profile, a substantially elliptical profile, a substantially parabolic profile, or any other similar profiles.

For purpose of clarity, it should be understood that the distal bone insertion part 210 may be inserted inside a first medullary cavity of the distal part of the ulna bone. In an implementation, distal bone insertion part 210 may be press-fitted into the first medullary cavity of the distal part of the ulna bone. However, in some alternative implementations, distal bone insertion part 210 may be cemented, adhered, screwed, or secured by other similar means to the distal part of the ulna bone. For example, in one implementation, a first lock screw may be used to secure the distal stem into a substantially fixed position inside the distal part of the ulna bone. Furthermore, distal bone insertion part 210 may be coated to provide a porous surface, into which the ulna bone will grow to help secure distal stem 202 in position.

In some exemplary implementations, proximal stem utilized in step 102 of the method 100 may be substantially similar to proximal stem 204. In some implementations, proximal stem 204 may include proximal bone insertion part 220 located at a proximal end of proximal stem 204. Proximal stem 204 may also include proximal base 222 located at a distal end of proximal stem 204. In some implementations, proximal bone insertion part 220 may include a circular profile. However, in some alternative implementations, proximal bone insertion part 220 may include a shape that having a substantially plug-shaped profile, a substantially elliptical profile, a substantially parabolic profile, or any other similar profiles. For purpose of clarity, it should be understood that proximal bone insertion part 220 maybe inserted inside a second medullary cavity of the proximal part of the ulna bone. In one implementation, distal bone insertion part 210 may be press-fitted into the second medullary cavity of the proximal part of the ulna bone. However, in some exemplary implementations, proximal bone insertion part 220 may be cemented, adhered, screwed, or secured by other similar means to the proximal part of the ulna bone. For example, in one implementation, a second lock screw may be used to secure the proximal stem into a substantially fixed position inside the proximal part of the ulna bone. Furthermore, proximal bone insertion part 220 may be coated to provide a porous surface, into which the ulna bone will grow to help secure proximal stem 204 in position.

Furthermore, proximal base 222 may include second outer band 224 comprising plurality of threaded holes 226. Proximal base 222 may further include plurality of screws 228 in which each respective screw in plurality of screws 228 may be associated with a respective threaded hole of plurality of holes 226, and also each respective threaded hole may be tightened by the insertion of the associated respective screw. In some implementations, proximal stem 204 may further include cylindrical-shaped opening 229 located at the distal end of proximal stem 204.

In an aspect, cylindrical-shaped opening 229 may be shaped to receive stem insertion part 230 of mobile locker 206. In some implementations, stem insertion part 230 may be located at a proximal end of mobile locker 206, and also a size of stem insertion part 230 may correspond to a size of cylindrical-shaped opening 229. For example, a diameter of stem insertion part 230 and a diameter of cylindrical-shaped opening 229 may correspond such that mobile locker 206 may be disposed rotatably, about axis 209, inside cylindrical-shaped opening 229. In some alternative exemplary implementations, stem insertion part 230 may include other shapes and consequently, cylindrical-shaped opening 229 may have a corresponding shape.

In some implementations, method 100 may further include an additional step that may be implemented before step 101. The additional step may comprise dividing the ulna bone into a proximal part and a distal part by removing a segment of the ulna bone, the proximal part connected to a proximal radioulnar joint and the distal part connected to a distal radioulnar joint. Referring again to FIG. 2A, it may be understood that according to some exemplary embodiments of the present disclosure, before implementing step 101 of the method 100, the ulna bone may be divided into distal part 242 and proximal part 240 by removing a segment 244 of the ulna bone. Accordingly, proximal stem 204 may be sized in order to be able to be inserted in proximal part 240, and distal part 202 may be sized in order to be able to be inserted into distal part 242. With regards to FIG. 2A, suffix "a" and "b" are used to show various views of a respective part. Views labeled 202a, 204a, and 206a are respectively the side views of distal stem 202, proximal stem 204, and mobile locker 206. Similarly views labeled 202b, 204b, and 206b are respectively the section views of distal stem 202, proximal stem 204, and mobile locker 206.

Furthermore, method 100 includes step 103 that comprises inserting a stem insertion part located at a proximal end of a mobile locker into the cylindrical-shaped opening of the proximal stem. As shown in FIGS. 2A and 2B, in some implementations, the mobile locker utilized in step 103 and step 104 of the method 100 may be substantially similar to a mobile locker 206.

In some implementations, mobile locker 206 may further include mobile locker base 232 located at a distal end of mobile locker 206. In an exemplary implementation, mobile locker base 232 may include second mobile globe holding section 234 comprising second half-spherical surface 236 with the largest exposed surface area at a proximal end of mobile locker 206. In some implementations, a size of second mobile globe holding section 234 may correspond to a size of mobile globe 208. For example, a diameter of second mobile globe holding section 234 may correspond to a diameter 250 of mobile globe 208, specifically the diameter of mobile globe 208 may be slightly smaller than the diameter of second mobile globe holding section 234. Mobile locker base 232 may further include third outer band 238 disposed at the distal end of the mobile locker 206 including second semicircle-shaped opening 239 from a side view perspective of second mobile globe holding section 234.

Figure 3:
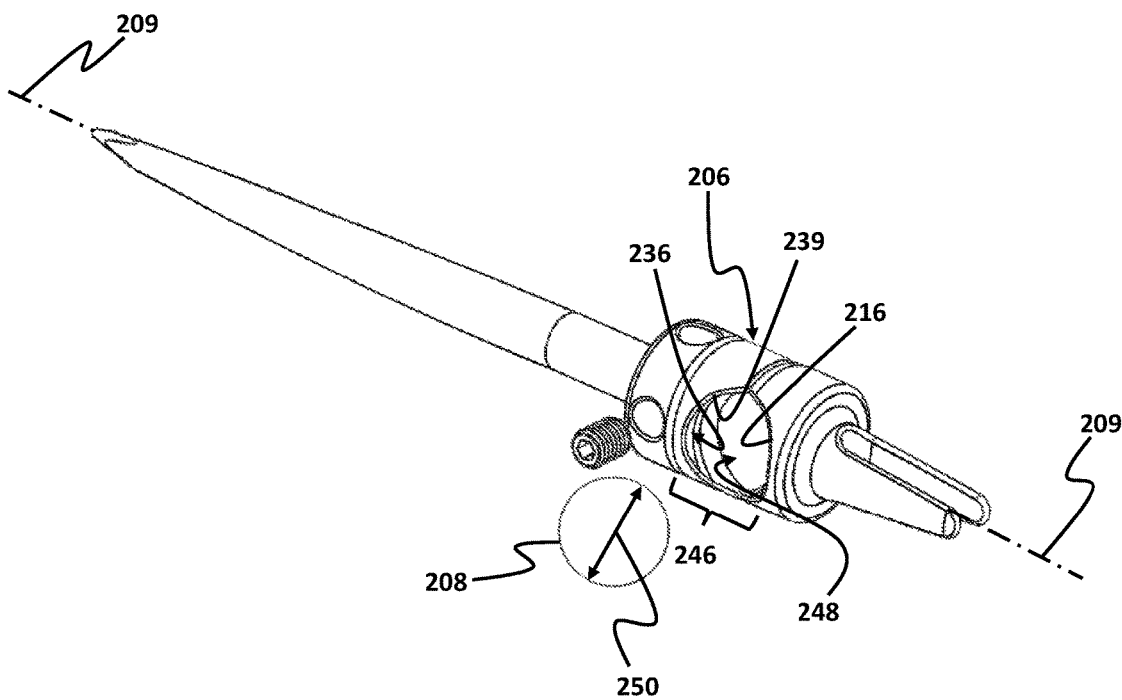
FIG. 3 illustrates a perspective view of an artificial prosthesis configured for receiving a mobile globe, consistent with one or more exemplary embodiments of the present disclosure.
Figure 4:
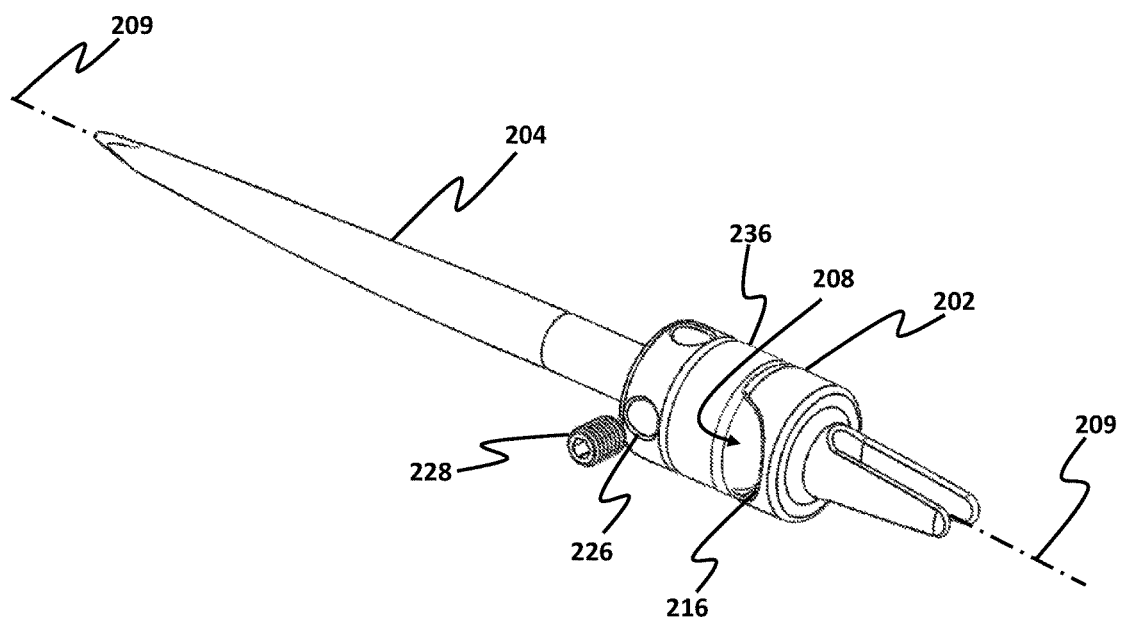
FIG. 4 illustrates a perspective view of an artificial prosthesis configured for trapping a mobile globe, consistent with one or more exemplary embodiments of the present disclosure.

Furthermore, method 100 includes step 104 comprising twisting the mobile locker so that the first semicircle-shaped opening and the second semicircle-shaped opening are aligned such that a spherical cavity is formed between the mobile locker and the distal stem, and step 105 comprising inserting a mobile globe into the spherical cavity. FIGS. 3 and 4, illustrate, graphically, an overview of various implementations of the artificial prosthesis 200, configured to operate together to provide some degrees of freedom for the forearm of the patient to be able to replace a distal radioulnar joint.

Referring now to FIG. 3, it may be understood that as mobile locker 206 is twisted around the axis 209 inside cylindrical-shaped opening 229 in a way such that first semicircle-shaped opening 216 is aligned with second semicircle-shaped opening 239, a full-circle opening 246, comprising first semicircle-shaped opening 216 and second semicircle-shaped opening 239, and spherical cavity 248, comprising first half-spherical surface (obscured from the view in FIG. 3) and second half-spherical surface 236 are formed. In some exemplary implementations, a size of the spherical cavity corresponds to a size of the mobile globe 208. For example, a diameter of an exemplary spherical cavity and a diameter of an exemplary full-circle opening 246 may be larger than a diameter of mobile globe 208 by the extent of approximately 200 µm. In an implementation, the full-circle opening 246 may aid in allowing the spherical cavity to receive and hold mobile globe 208.

Method 100 may further include step 106 comprising twisting the mobile locker so that the first semicircle-shaped opening and the second semicircle-shaped opening are misaligned and the mobile globe is secured within the spherical cavity. Referring now to FIG. 4, it may be understood that responsive to an arrangement in which mobile locker 206 is twisted around the 209 inside the cylindrical-shaped opening (labeled 229 in FIG. 2B but obscured from the view in FIG. 4), for example by amount of 180 degrees, in a way such that the first semicircle-shaped opening 216 is misaligned with the second semicircle-shaped opening (labeled 239 in FIG. 2B but obscured from the view in FIG. 4), the full-circle opening 246 may be obliterated and consequently mobile globe 208 is prevented from going out from the spherical cavity. Trapping the mobile globe 208 inside the spherical cavity may provide significant benefits, including but not limited to, maintaining the distal stem 202 and the proximal stem 204 aligned with each other in direction of the axis 209, in other words, trapping the mobile globe 208 inside the spherical cavity may aid in fixing the main axis of the distal stem 202 and the proximal stem 204 to axis 209.

In an exemplary embodiment, once the mobile globe 208 is inserted into the spherical cavity from the full-circle opening 246, the mobile locker 206 may be twisted around axis 209 inside the cylindrical-shaped opening (labeled 229 in FIG. 2B but obscured from the view in FIG. 3) in a way such that first semicircle-shaped opening 216 is misaligned with second semicircle-shaped opening 239. For example, mobile locker 206 may be twisted around axis 209 inside the cylindrical-shaped opening (labeled 229 in FIG. 2B but obscured from the view in FIG. 3) 180 degrees. Furthermore, in some implementations, once mobile locker 206 is twisted around axis 209 inside cylindrical-shaped opening (labeled 229 in FIG. 2B but obscured from the view in FIG. 3) and consequently first semicircle-shaped opening 216 and second semicircle-shaped opening 239 are misaligned, plurality of screws 228 may be tightened inside plurality of threaded holes 226 to minimize movements of mobile locker 206.

According to some exemplary implementations, method 100 may include step 107 comprising securing the mobile locker into a substantially fixed position relative to the proximal stem by tightening one or more of the plurality of screws in the plurality of threaded holes.

With further reference to FIG. 2B, it may be understood that movements of mobile locker 208 inside cylindrical-shaped opening 229 may be minimized or otherwise prevented due to tightening of plurality of screws 228 inside plurality of threaded holes 226. However, in some exemplary implementations, securing the mobile locker 208 into a substantially fixed position relative to the proximal stem 204 may be done by any other securing mechanism with similar functionality.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 202, 204, or 206 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study, except where specific meanings have otherwise been set forth herein. Relational terms such as "first" and "second" and the like may be used solely to distinguish one entity or action from another without necessarily requiring or implying any actual such relationship or order between such entities or actions. The terms "comprises," "comprising," or any other variation thereof, as used herein and in the appended claims are intended to cover a non-exclusive inclusion, encompassing a process, method, article, or apparatus that comprises a list of elements that does not include only those elements but may include other elements not expressly listed to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is not intended to be used to interpret or limit the scope or meaning of the claims. In addition, in the foregoing Detailed Description, it can be seen that various features are grouped together in various implementations. Such grouping is for purposes of streamlining this disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into this Detailed Description, with each claim standing on its own as a separately claimed subject matter.

While various implementations have been described, the description is intended to be exemplary, rather than limiting and it will be apparent to those of ordinary skill in the art that many more implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:
1. An artificial prosthesis, comprising:
a mobile globe comprising a metallic spherical structure;
a distal stem, comprising:
  a distal bone insertion part located at a distal end of the distal stem; and
  a distal base, the distal base comprising:
    a first mobile globe holding section, the first mobile globe holding section comprising a first half-spherical surface with a largest circumference at a proximal end of the distal stem; and
    a first outer band located at the proximal end of the distal stem including a first semicircle-shaped opening from a side-view perspective of the first mobile globe holding section;
a proximal stem, including:
  a proximal bone insertion part located at a proximal end of the proximal stem;
  a proximal base located at a distal end of the proximal stem, the proximal base comprising:
    a second outer band comprising a plurality of threaded holes;
    a plurality of screws, each respective screw in the plurality of screws associated with a respective threaded hole of the plurality of holes, each respective threaded hole configured to be tightened by the insertion of the associated respective screw;
    a cylindrical-shaped opening located at the distal end of the proximal stem;
a mobile locker including:
  a stem insertion part located at a proximal end of the mobile locker, a size of the stem insertion part corresponding to a size of cylindrical-shaped opening;
  a mobile locker base located at a distal end of the mobile locker, the mobile locker base comprising:
    a second mobile globe holding section comprising a second half-spherical surface with the largest exposed surface area at a proximal end of the mobile locker; and
    a third outer band disposed at the distal end of the mobile locker including a second semicircle-shaped opening from a side view perspective of the second mobile globe holding section;
wherein a spherical cavity is formed between the mobile locker and the distal stem in an arrangement in which the first semicircle-shaped opening and the second semicircle-shaped opening are aligned, the spherical cavity shaped to receive and hold the mobile globe; and
wherein the distal stem and the mobile locker are positioned to retain the mobile globe within the spherical cavity in an arrangement in which the first semicircle-shaped opening and the second semicircle-shaped opening are misaligned.

2. The artificial prosthesis of claim 1, wherein the mobile globe, the distal stem, the proximal stem, and the mobile locker are manufactured from one of cobalt-chromium alloy, titanium, and stainless steel.

3. The artificial prosthesis of claim 1, wherein a difference between the mobile globe diameter and respective diameters of the first semicircle-shaped opening and the second semicircle-shaped opening is in the range of 100 μm to 1 mm.

4. The artificial prosthesis of claim 1, wherein the proximal bone insertion part has a shape that comprises one of substantially circular profile, substantially elliptical profile, substantially parabolic profile, and plug-shaped profile.

5. A method for implanting an artificial prosthesis, the method comprising:
  inserting a distal stem into a distal part of the ulna bone, the distal stem comprising:
    a distal bone insertion part located at a distal end of the distal stem; and
    a distal base, the distal base comprising:
      a first mobile globe holding section, the first mobile globe holding section comprising a first half-spherical surface with the largest circumference at a proximal end of the distal stem; and
      a first outer band located at the proximal end of the distal stem including a first semicircle-shaped opening from a side-view perspective of the first mobile globe holding section;
  inserting a proximal stem into the proximal part of the ulna bone, the proximal stem comprising:
    a proximal bone insertion part located at a proximal end of the proximal stem;
    a proximal base located at a distal end of the proximal stem, the proximal base comprising:
      a second outer band comprising a plurality of threaded holes;
      a plurality of screws, each respective screw in the plurality of screws associated with a respective threaded hole of the plurality of holes, each respective threaded hole configured to be tightened by the insertion of the associated respective screw;
      a cylindrical-shaped opening located at the distal end of the proximal stem;
  inserting a stem insertion part located at a proximal end of a mobile locker into the cylindrical-shaped opening of the proximal stem, a size of the stem insertion part corresponding to a size of cylindrical-shaped opening, the mobile locker further comprising:
    a mobile locker base located at a distal end of the mobile locker, the mobile locker base comprising:
      a second mobile globe holding section comprising a second half-spherical surface with the largest exposed surface area at a proximal end of the mobile locker; and
      a third outer band disposed at the distal end of the proximal stem including a second semicircle-shaped opening from a side view perspective of the second mobile globe holding section;
  twisting the mobile locker so that the first semicircle-shaped opening and the second semicircle-shaped opening are aligned such that a spherical cavity is formed between the mobile locker and the distal stem;
  inserting a mobile globe into the spherical cavity, the mobile globe comprising a metallic spherical structure;
  twisting the mobile locker so that the first semicircle-shaped opening and the second semicircle-shaped opening are misaligned and the mobile globe is secured within the spherical cavity; and
  securing the mobile locker into a substantially fixed position relative to the proximal stem by tightening one or more of the plurality of screws in the plurality of threaded holes.

6. The method of claim 5, further comprising dividing the ulna bone into the proximal part and the distal part by removing a segment of the ulna bone, the proximal part connected to a proximal radioulnar joint and the distal part connected to a distal radioulnar joint.

7. The method of claim 6, further comprising securing the distal stem into a substantially fixed position inside the distal part of the ulna bone by tightening a first lock screw.

8. The method of claim 7, further comprising securing the proximal stem into a substantially fixed position inside the proximal part of the ulna bone by tightening a second lock screw.

9. The method of claim 6, wherein a length of the segment of the ulna bone is in the range of 1.6 cm to 2.8 cm.

10. The method of claim 6, wherein the mobile globe, the distal stem, the proximal stem, and the mobile locker are manufactured from one of cobalt-chromium alloy, titanium alloys, and stainless steel.

11. The method of claim 6, wherein a difference between the mobile globe diameter and respective diameters of the first semicircle-shaped opening and the second semicircle-shaped opening is in the range of 200 μm to 1 mm.

12. The method of claim 6, wherein the proximal bone insertion part has a shape that comprises one of substantially circular profile, substantially elliptical profile, substantially parabolic profile, and plug-shaped profile.

* * * * *